United States Patent [19]

Kaiser et al.

[11] 3,933,859

[45] Jan. 20, 1976

[54] DIHYDROCOUMARIN DERIVATIVES

[75] Inventors: Ado Kaiser, Neu-Frenkendorf; Wolfgang Koch, Riehen; Marcel Scheer, Basel; Uwe Wolcke, Bottmingen, all of Switzerland

[73] Assignee: Hoffmann-La Roche, Inc., Nutley, N.J.

[22] Filed: June 12, 1974

[21] Appl. No.: 478,654

Related U.S. Application Data

[62] Division of Ser. No. 191,358, Oct. 21, 1971, abandoned.

[30] Foreign Application Priority Data

Oct. 30, 1970 Switzerland................. 16041/70

[52] U.S. Cl......... 260/343.2 R; 260/340.7; 260/404; 260/471 A; 260/514 R; 260/519; 260/520; 424/279; 424/282; 424/319
[51] Int. Cl.²...................................... C07D 311/20
[58] Field of Search ............................ 260/343.2 R

[56] References Cited

OTHER PUBLICATIONS

Langley et al., Chem. Abstracts, Vol. 17, (1923), 85–86.
Kawai et al., Chem. Abstracts, Vol. 46, (1952), 8809f.
Langemann et al., Chem. Abstracts, Vol. 71, (1969), 22316a.

*Primary Examiner*—James A. Patten
*Attorney, Agent, or Firm*—Samuel L. Welt; Jon S. Saxe; George M. Gould

[57] ABSTRACT

Process for obtaining 5,6 or 6,7 or 7,8 dihydroxy coumarin or derivatives thereof, which are useful for lower blood pressure and for chemical sympathectomy by oxidizing 2,3 or 3,4 or 4,5 dihydroxyphenylpropionic acid or derivatives thereof, and novel coumarin derivatives of the process.

4 Claims, No Drawings

DIHYDROCOUMARIN DERIVATIVES

This is a division of application Ser. No. 191,358 filed Oct. 21, 1971, now abandoned.

SUMMARY OF THE INVENTION

In accordance with the process of this invention, a compound of the formula:

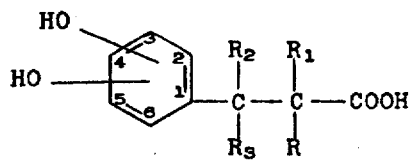

I wherein R is hydrogen, lower alkyl or acylamino; $R_1$, $R_2$ and $R_3$ are hydrogen or lower alkyl; and the hydroxy groups are ortho to one another; is oxidized to form a compound of the formula:

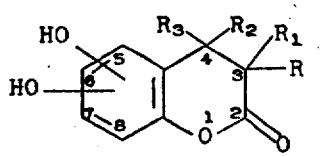

II wherein R, $R_1$, $R_2$ and $R_3$ are as above; and the hydroxy groups are ortho to one another.

The resulting coumarin derivative of formula II is then acylated, alkylated, cycloalkylated, alkenylated, alkynylated or alkylenated to a compound of the formula:

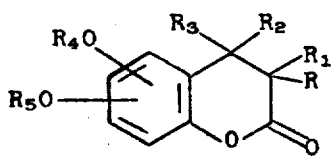

III wherein R, $R_1$, $R_2$ and $R_3$ are as above; $R_4$ and $R_5$ are individually acyl, alkyl, cycloalkyl, alkenyl or alkynyl or $R_4$ and $R_5$ taken together form an alkylene group; and $-OR_4$ and $-OR_5$ are ortho to one another.

The coumarin derivative of formulae II or III, having the formula:

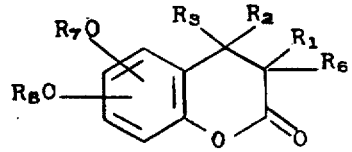

IV wherein $R_1$, $R_2$ and $R_3$ are as above, $R_6$ is carbobenzoxyamino or tertbutoxycarbonylamino; $R_7$ and $R_8$ are individually hydrogen, acyl, alkyl, cycloalkyl, alkenyl or alkynyl or $R_7$ and $R_8$ taken together form an alkylene group; and $-OR_7$ and $-OR_8$ are ortho to one another: is then converted in a manner known per se to a compound of the formula:

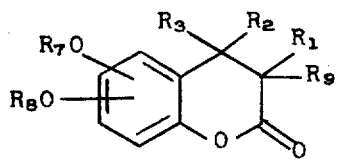

V wherein $R_1$, $R_2$, $R_3$, $R_7$ and $R_8$ are as above and $R_9$ is amino.

In accordance with another embodiment of this invention, a compound of the formula:

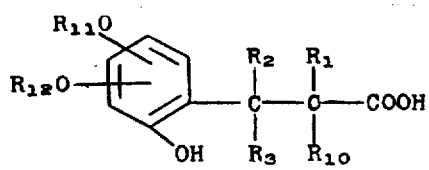

VI wherein $R_1$, $R_2$, $R_3$ are as above; $R_{10}$ is hydrogen, amino, lower alkyl or acylamino; $R_{11}$ and $R_{12}$ are hydrogen, alkyl, cycloalkyl, alkenyl or alkynyl or $R_{11}$ and $R_{12}$ taken together form an alkylene group; and $-OR_{11}$ and —$OR_{12}$ are ortho to one another; is obtained by the hydrolysis of a compound of formulae II, III, or V.

The compounds of formulae II, III, V, or VI can then be converted into their addition salts by treatment with an acid or a base.

In accordance with still another embodiment of this invention, novel compounds selected from the group consisting of compounds of the formulae:

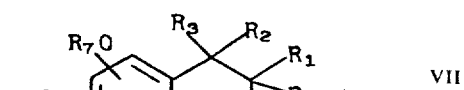

VII and

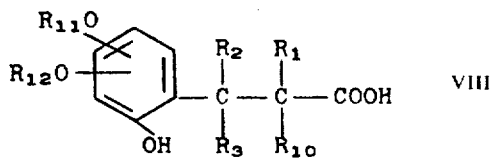

VIII wherein $R_1$, $R_2$, $R_3$, $R_7$, $R_8$, $R_{10}$, $R_{11}$ and $R_{12}$ are as above; $-OR_7$ and $-OR_8$ are ortho to one another; and $-OR_{11}$ and $-OR_{12}$ are ortho to one another; with the provisos that when $R_2$, $R_3$, $R_7$ and $R_8$ are hydrogen, $R_1$ is hydrogen or methyl and $R_{10}$ is hydrogen or amino, then $-OR_7$ is in either the 5- or 8-position and when $R_2$, $R_3$, $R_{11}$ and $R_{12}$ are hydrogen, $R_1$ is hydrogen or methyl and $R_{10}$ is hydrogen or amino, then $-OR_{11}$ is in either the 3- or 6-position; and addition salts thereof with acids or bases, are produced by the process of this invention. These compounds are useful for lowering blood-pressure and for chemical sympathectomy.

DETAILED DESCRIPTION OF THE INVENTION

As used throughout this application, the term "acyl" denotes an alkanoyl, alkenoyl, alkynoyl, aroyl or aralkanoyl group. Alkanoyl groups contain 1 to 18 carbon atoms and can be straight-chain or branched-chain. They can also carry substituents such as, for example, hydroxy or lower alkoxy groups. Examples of such alkanoyl groups are the formyl, acetyl, propionyl, butyryl, isobutyryl, valeryl, hexanoyl, heptanoyl, decanoyl and like groups. Alkenoyl groups can be straight-chain or branched-chain groups containing 2 to 18 carbon atoms and one or more double bonds. They can also carry substituents such as, for example, an aryl or a lower alkoxy-substituted aryl group. Examples of such alkenoyl groups are the acryloyl, crotonyl, α-methylcrotonyl and like groups. Alkynoyl groups can be straight-chain or branched-chain groups containing 2 to 18 carbon atoms and one or more triple bonds. They may, in addition, contain one or more double bonds. Examples of such alkynoyl groups are the propiolyl, methylpropiolyl and like groups. Aroyl groups are especially the benzoyl group and lower alkyl-, lower alkoxy-, nitro- or halo-substituted benzoyl groups such as, for example, the o-, m- or p-methoxy-, nitro- or chloro-benzoyl and like groups. Aralkanoyl groups are especially unsubstituted or substituted phenylalkanoyl groups containing 2 to 18 carbon atoms in the alkanoyl group such as, for example, phenacetyl, phenylpropionyl and like groups. The phenyl ring can be substituted by, for example, halogen, nitro, lower alkyl or lower alkoxy. Aryl groups are especially the phenyl group and hydroxy-, halogen-, nitro-, lower alkyl- or lower alkoxy-substituted phenyl groups. Acylamino groups are amino groups in which one hydrogen atom has been replaced by an alkanoyl, alkenoyl, alkynoyl, aralkanoyl, alkoxycarbonyl or aralkoxycarbonyl group. The alkyl residue of the alkoxycarbonyl groups contains 1 to 8 carbon atoms and can be straight-chain or branched-chain. Examples of such alkoxycarbonyl groups are the methoxycarbonyl, propoxycarbonyl, butoxycarbonyl, tertbutoxycarbonyl and like groups. Aralkoxycarbonyl groups are especially phenylalkoxycarbonyl groups containing 1 to 8 carbon atoms in the alkoxycarbonyl group such as, for example, the benzyloxycarbonyl, phenylpropyloxycarbonyl and like groups. The term "lower alkyl" means straight-chain or branched-chain alkyl groups containing 1 to 7 carbon atoms such as, for example, methyl, ethyl, n-propyl, isopropyl, butyl, tertbutyl, hexyl and the like, with methyl being preferred. The terms "alkyl, alkenyl and alkynyl" mean straight-chain or branched-chain saturated or unsaturated hydrocarbon groups as the case may be containing 1 to 15 carbon atoms, such as, for example, methyl, ethyl, n-propyl, isopropyl, n-butyl, tertbutyl, octyl, pentyl, vinyl, allyl, propynyl, butynyl and the like. The term "alkylene" means the methylene group and polymethylene groups containing 1 to 8 carbon atoms. The term "cycloalkyl" means cyclic, saturated hydrocarbyl groups containing 3 to 6 carbon atoms such as cyclopropyl, cyclohexyl and the like.

It will be appreciated that the expression "in a manner known per se" is used in this description to mean methods and process steps in actual use for or described in the literature on the subject.

In accordance with the process of this invention, the compound of formula II is obtained by treating the compound of formula I with an oxidizing agent. In this reaction, any conventional oxidizing agent can be utilized, such as silver oxide, molecular oxygen, manganese dioxide, potassium ferricyanide, hydrogen peroxide, Fremi salt, iodoso-benzene, iodoso-benzene diacetate, 2,3-dichloro-5,6-dicyano-p-benzoquinone, 1,2,3,4-tetrachloro-o-benzoquinone and the like. The oxidation proceeds via an o-quinone of the general formula:

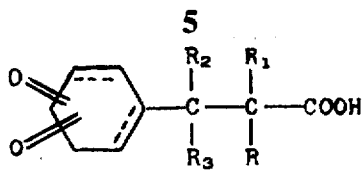

IX wherein R, $R_1$, $R_2$ and $R_3$ are as above and the broken lines signify carbon to carbon bonds corresponding to the quinone structure; with the proviso that the oxo groups are ortho to one another; which is formed as an intermediate.

In carrying out the oxidation, the amount of oxidizing agent utilized is not critical. Preferably, only the minimum amount of oxidizing agent required for the oxidation of the catechol grouping to the quinone is utilized, so as to avoid the further oxidation of the hydroxy groups in the compound of formula II. The oxidation is accordingly preferably carried out in an inert gas atmosphere such as, for example, under nitrogen, carbon dioxide, argon and the like. The oxidation is also preferably carried out in an inert organic-solvent. In this reaction, any conventional inert organic solvent may be utilized, such as a lower alkanecarboxylic acid, preferably formic acid, glacial acetic acid and propionic acid; an ether, preferably diethyl ether, dioxane and tetrahydrofuran; a lower alkanol, preferably ethanol; or a lower ketone, preferably acetone. In carrying out the oxidation reaction, temperature and pressure are not critical and the reaction can be suitably carried out at a temperature of about $-20°$ C. to about 100°C. and at atmospheric pressure, with about room temperature being preferred. Furthermore, the oxidation can be carried out in the absence of or in the presence of a catalyst. Among the catalysts which may be utilized in this reaction, the acidic catalysts are preferred, particularly p-toluenesulphonic acid, gaseous hydrogen chloride, sulphuric acid, trifluoroacetic acid and the like, as well as Lewis acids such as boron trifluoride, aluminum chloride, titanium tetrachloride and the like.

The acylation, alkylation, cycloalkylation, alkenylation, alkynylation or alkylenation of a compound of formula II, obtained by oxidation, can be carried out in a manner known per se, for example, by reaction with a compound furnishing the group $R_4$ or $R_5$. Acyl groups can be introduced, for example, by reaction with a corresponding acyl halide such as a bromide or chloride, an acyl anhydride, an activated ester or acid azide or the like. Alkyl, alkenyl, alkynyl and cycloalkyl groups can be introduced, for example, by reaction with the corresponding halides, preferably the bromides or chlorides. Alkylene groups can be introduced, for example, by reaction with corresponding $\omega,\omega'$-dihaloalkyl compounds such as 1,2-dibromoethane, 1,3-dibromopropane and the like.

The conversion of the compound of formula IV to the compound of formula V can be carried out in a manner known per se, for example, the carbobenzoxyamino group or the tertbutoxycarbonylamino group can be converted to an amino group by treatment with a hydrogen halide such as hydrogen bromide or chloride or by hydrogenation in the presence of a catalyst such as, for example, palladium/charcoal. During such a hydrogenation, unsaturated groups which may be present in the molecule are also hydrogenated.

The hydrolysis of the compounds of formulae II, III, or V to form the compound of formula VI can be carried out in a conventional manner. Preferably, the hydrolysis is carried out in water or in a water miscible organic solvent and in an inert gas atmosphere. In this reaction, any conventional, water miscible solvent can be utilized, such as tetrahydrofuran, dioxane, acetonitrile, etc. Among the inert gases which can be utilized are the gases set forth above. In carrying out this reaction, temperature and pressure are not critical, and in general the hydrolysis can be carried out at from 0°C. to the reflux temperature of the mixture. The conditions employed for the hydrolysis are preferably modified depending upon whether an N-acyl group is to be retained. When an N-acyl group, which is present, is to be retained, the hydrolysis is preferably carried out under mild conditions, particularly at a pH of from about 2 to about 8. When an N-acyl group which is present is to be hydrolyzed off, more rigorous conditions are preferably employed, for example 1-4 N aqueous mineral acids such as hydrochloric acid, sulphuric acid and the like are used. The hydrolysis can be carried out under acidic or under alkaline conditions, for example, by means of an alkali metal hydroxide or hydrochloric acid, sulphuric acid and the like. Acyl groups which may be present on the phenyl ring are cleaved off during the hydrolysis in each case.

Those compounds of formulae I–VIII which contain an asymmetric carbon atom can exist in the form of racemates which can be resolved into the optical antipodes in a manner known per se, for example, by means of an optically active base.

The compounds of formulae II, III, V, VII and VIII form addition salts when treated with acids or with bases. In forming acid addition salts, there can be used any pharmaceutically acceptable organic or inorganic acid such as, for example, acetic acid, oxalic acid, hydrochloric acid and the like. In forming base addition salts, there can be used any conventional, pharmaceutically acceptable organic or inorganic base such as, for example, the alkali metal hydroxides, particularly sodium and potassium hydroxides, and ammonium hydroxide.

The compounds of formula I, used as the starting materials in the process of this invention, are in part new and in part known compounds.

The known compounds of formula I can be prepared according to methods which are known per se.

The new compounds of formula I can be prepared in a manner analogous to that used for the preparation of the known compounds. Compounds of formula I in which R is acylamino can be prepared, for example, by acylating a compound of the formula:

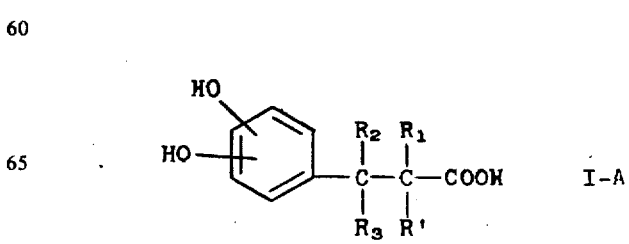

I-A wherein $R_1$, $R_2$, $R_3$ are as above, R' is amino; and the hydroxy groups are ortho to one another.

In this acylation, the amino compound of formula I-A can be treated with borax under an inert gas atmosphere in an aqueous alkaline medium to yield a boric acid complex in which the two phenolic hydroxy groups are esterified with boric acid. In carrying out the treatment with borax, temperature and pressure are not critical. Preferably, the treatment is carried out at a temperature of from about 0°C. to about 70°C. and at a pH of from about 7 to 11. The boric acid complex can subsequently be reacted with an agent furnishing the desired acid group, for example, a corresponding acid halide, preferably a bromide or chloride, an acid anhydride or acid azide. In carrying out this reaction with an acid group, the reaction medium, temperature and pH are preferably the same as employed in the preparation of the boric acid complex above. The N-acylated boric acid complex can subsequently be cleaved by acidification in an aqueous medium.

Among the preferred starting materials of formula I are included the compounds wherein the hydroxy groups are present in the 3,4-position. Starting materials of formula I in which R represents the carbobenzoxyamino or tertbutoxycarbonylamino group are also preferred. Examples of preferred starting materials of formula I are:

hydrocaffeic acid;
N-formyl-3-(3,4-dihydroxyphenyl)-L-alanine;
N-acetyl-3-(3,4-dihydroxyphenyl)-L-alanine;
N-(tertbutoxycarbonyl)-3-(3,4-dihydroxyphenyl)-L-alanine;
N-(benzyloxycarbonyl)-3-(3,4-dihydroxyphenyl)-L-alanine;
N-(benzyloxycarbonyl)-D,L-α-methyl-3,4-dihydroxyphenylalanine; and
D,L-α-methyl-3-(3,4-dihydroxyphenyl)-propionic acid.

The novel compounds of formulae VII and VIII and their salts are useful for lowering the blood-pressure and for chemical sympathectomy. Thus, for example, after orally administering five separate doses each comprising 300 μmol/kg of L-6,7-diacetoxy-3-aminohydrocoumarin hydrochloride to rats over a period of 48 hours, the noradrenaline content is lowered in the heart to 28% and in the brain to 85% of the controls. The $LD_{50}$ of this hydrochloride amounts to 30–60 mg/kg i.v., 250–500 mg/kg s.c. and 1,000–2,000 mg/kg p.o.

The novel compounds of formula VII and their salts also have a cholesterol-lowering activity.

Among the preferred compounds of formula VII are the compounds wherein —$OR_7$ and —$OR_8$ are in the 6,7-position. Also among the preferred compounds of formula VII are the compounds wherein $R_4$ and $R_5$ are acyl. Further among the preferred compounds of formula VII are the compounds wherein $R_{10}$ is carbobenzoxyamino or tertbutoxycarbonylamino. Among the particularly preferred compounds of formula VII are:

L-3-formamido-6,7-dihydroxyhydrocoumarin;
L-3-acetamido-6,7-dihydroxyhydrocoumarin;
L-3-(1-tertbutoxyformamido)-6,7-dihydroxyhydrocoumarin;
L-3-[1-(benzyloxy)-formamido]-6,7-dihydroxyhydrocoumarin;
L-3-(1-tertbutoxyformamido)-6,7-diacetoxyhydrocoumarin;
L-6,7-diacetoxy-3-aminohydrocoumarin;
D,L-3-[1-(benzyloxy)-formamido]-3-methyl-6,7-dihydroxyhydrocoumarin;
D,L-6,7-diacetoxy-3-methylhydrocoumarin;
L-3-(1-tertbutoxyformamido)-6,7-dibenzoyloxyhydrocoumarin;
L-3-amino-6,7-dibenzoyloxyhydrocoumarin;
D,L-3,4,4-trimethyl-3-N-benzyloxycarbonylamino-6,7-dihydroxyhydrocoumarin;
D,L-6,7-diacetoxy-3-N-benzyloxycarbonylamino-3,4,4-trimethylhydrocoumarin; and
D,L-6,7-diacetoxy-3-amino-3,4,4-trimethylhydrocoumarin;
and salts thereof.

Among the preferred compounds of formula VIII are compounds in which the groups —$OR_{11}$ and —$OR_{12}$ are in the 4,5-position, especially those in which $R_{11}$ and $R_{12}$ each represent a hydrogen atom. Also preferred are those compounds of formula VIII in which $R_{10}$ is acylamino.

The compounds of formulae VII and VIII and their salts can be used as medicaments in the form of pharmaceutical preparations which contain them in association with a compatible pharmaceutical carrier. This may be an organic or inorganic inert carrier material which is suitable for enteral or parenteral administration such as, for example, water, gelatin, gum arabic, lactose, starches, magnesium stearate, talc, vegetable oils, polyalkylene glycols, petroleum jelly, etc. The pharmaceutical preparations can be made up in solid form (e.g. as tablets, dragees, suppositories or capsules) or in liquid form (e.g. as solutions, suspensions or emulsions). They may be sterilized and/or may contain adjuvants such as preserving, stabilizing, wetting or emulsifying agents, and salts for varying the osmotic pressure or buffers. They can also contain other therapeutically valuable substances.

The following Examples illustrate the present invention.

EXAMPLE 1

7.5 g of hydrocaffeic acid, 13.5 g of iodoso-benzene diacetate and 150 ml of glacial acetic acid are stirred at room temperature (22°C.) under an argon atmosphere. After 2 hours, 0.5 g of p-toluenesulphonic acid is added. The solution thereupon becomes black-red in color and warms to 30°C. After a further 3 hours, the mixture is evaporated at 40°C/12 mmHg and the residue is recrystallized once from ethyl acetate and twice from water. There is obtained 2.5 g of 6,7-dihydroxyhydrocoumarin of melting point 212°C. (decomposition).

EXAMPLE 2

11 g of n-formyl-3-(3,4-dihydroxyphenyl)-L-alanine is dissolved with shaking in 120 ml of glacial acetic acid. To the solution there is added 14 g of iodosobenzene diacetate, which is likewise dissolved with shaking. The dark-red mixture, which becomes warm, is allowed to stand overnight. On the next day, it is filtered, the filtrate evaporated at 40°C/12 mmHg and evaporated again with the addition of toluene. The residue is extracted three times with 100 ml of hot ethyl acetate each time, and the extracts are evaporated. The crude product thus obtained is recrystallized once from ethyl acetate and once from glacial acetic acid with the addition of active charcoal. There is obtained 1.5 g of L-3-formamido-6,7-dihydroxyhydrocoumarin of melting point 244°–245°C. (decomposition); $[\alpha]_D^{25} = -24.4°$ (c = 1%, dimethyl sulphoxide).

EXAMPLE 3

16.1 of iodoso-benzene diacetate is added in one portion to a solution of 23.9 g of N-acetyl-3-(3,4-dihydroxyphenyl)-L-alanine in 250 ml of glacial acetic acid. The mixture immediately becomes deep-red in color, and the temperature rises to 30°C. The mixture is held at room temperature for 24 hours, filtered and then evaporated at 40°C/12 mmHg. The red oily residue is partitioned between tetrahydrofuran-ethyl acetate (2:5 parts by volume) and saturated aqueous sodium chloride solution. The organic phases are washed with saturated aqueous sodium chloride solution, exhaustively extracted with saturated aqueous sodium bicarbonate solution and then, after drying over sodium sulphate, evaporated under vacuum. The residue is recrystallized from glacial acetic acid with the addition of active charcoal. 2.2 g of L-3-acetamido-6,7-dihydroxyhydrocoumarin is obtained as colorless crystals of melting point 221°–224°C (decomposition); $[\alpha]_D^{25} = -30°$ (c = 1.038%, dimethyl sulphoxide).

EXAMPLE 4

7.7 g of 3-(3,4-dihydroxyphenyl)-L-alanine is added with stirring in an argon atmosphere to a suspension of 14.0 g of borax in 70.0 ml of water. The mixture is stirred for 15 minutes and then brought to pH 10 (pH meter) with 2-N aqueous sodium hydroxide. A boric acid complex forms, in which the hydroxyl groups on the phenyl ring of the alanine derivative are esterified with boric acid. Subsequently, 9.5 ml of acetic anhydride is added dropwise in the course of 2 hours at a temperature between 5°c. and 10°C. (cooling with an ice-bath), the pH of the mixture being held between 10 and 10.5 by the dropwise addition of 2-N sodium hydroxide. The mixture is stirred for a further 40 minutes at 20°–23°C., cooled to ca +5°C., and filtered off from the undissolved white crystals. The filtrate is brought to pH 1 with concentrated sulphuric acid and extracted three times with 600 ml of ethyl acetate each time. The extracts are dried over sodium sulphate and evaporated under vacuum. The residue is dissolved in a small amount of ethyl acetate, a small amount of white crystals (boric acid) remaining undissolved. The mixture is filtered, again evaporated under vacuum and the residue dried under an oil-pump vacuum at a bath temperature of 70°C. for 2 hours. There is thus obtained 9.22 g of crude N-acetyl-3-(3,4-dihydroxyphenyl)-L-alanine in the form of a light-beige, solid form; $[\alpha]_D^{25} = +42.6°$ (c = 0.82%, methanol).

EXAMPLE 5

16.2 g of iodoso-benzene diacetate is added in one portion with stirring in a nitrogen atmosphere to a solution of 15 g of N-(tertbutoxycarbonyl)-3-(3,4-dihydroxyphenyl)-L-alanine in 250 ml of glacial acetic acid, the mixture immediately becoming deep red-brown in color. After stirring at room temperature for 20 hours, the solution is evaporated at 40°C/12 mmHg. The residue is taken up in 800 ml of diethyl ether and filtered off from a small amount of undissolved, tarry material The filtrate is successively washed three times with 100 ml of water each time, three times with 100 ml of satu-rated aqueous sodium bicarbonate solution each time and once with 100 ml of water. After drying over sodium sulphate with the addition of active charcoal, the combined organic extracts are evaporated at 30°C/12 mmHg, 200 ml of absolute toluene being added. After two recrystallizations from toluene/diethyl ether, the crystalline residue yields 5.2 g of L-3-(1-tertbutoxyformamido)-6,7-dihydroxyhydrocoumarin of melting point 173°–176° C. (decomposition); $[\alpha]_D^{25} = -41°$ (c = 1%, ethanol).

EXAMPLE 6

2-N aqueous sodium hydroxide is added in an argon atmosphere to a mixture of 100 g of 3-(3,4-dihydroxyphenyl)-L-alanine, 200 g of borax and 1000 ml of water, up to pH 9.5 (pH meter). A boric acid complex forms, in which the hydroxyl groups on the phenyl ring of the alanine derivative are esterified with boric acid. Half of the crude tertbutoxycarbonyl azide prepared from 120 g of tertbutoxycarbonyl hydrazide is then added in one portion, and the mixture is stirred at room temperature for 6 hours, the pH being held between 9.3 and 9.8 by the occasional addition of 2-N aqueous sodium hydroxide. The remaining tertbutoxycarbonyl azide is subsequently added and the mixture is stirred for a further 14 hours. After 14 hours, the pH falls to 8.5. It is then brought to pH 9.5 with 2-N aqueous sodium hydroxide, and the mixture is stirred for a further 2 hours. The mixture is then extracted twice with 300 ml of diethyl ether each time. The aqueous phase is brought to pH 2.5 with 10% aqueous citric acid solution, saturated with sodium chloride, and extracted twice with 300 ml of ethyl acetate each time. The combined organic extracts are washed 10 times with 500 ml of water each time, dried over sodium sulphate and then concentrated under vacuum. The glassy residue crystallizes on digesting with cyclohexane. After two recrystallizations from ethyl acetate/cyclohexane, there is obtained 100 g of N-(tertbutoxycarbonyl)-3-(3,4-dihydroxyphenyl)-L-alanine of melting point 148°C.; $[\alpha]_D^{25} = +16.4°$ (c = 1%, methanol)

EXAMPLE 7

64.4 g of iodoso-benzene diacetate and 800 ml of p-toluenesulphonic acid are added in one portion with stirring to a solution of 73 g of crude N-(benzyloxycarbonyl)-3-(3,4-dihydroxyphenyl)-L-alanine in 1000 ml of glacial acetic acid (analytical grade). The mixture immediately becomes dark-red in color and warms to ca 30°C. It is subsequently stirred at room temperature for a further 15 hours. This clear, deep-red solution is then concentrated at 40°C/12 mmHg. The residue is taken up in 800 ml of ethyl acetate, and the solution is successively washed twice with 400 ml of ice-cold, saturated aqueous sodium chloride solution each time, four times with 400 ml of ice-cold saturated aqueous sodium carbonate solution each time and once with 400 ml of ice-cold saturated aqueous sodium chloride solution. The aqueous extracts are back-extracted with 800 ml of ethyl acetate. The organic phases are combined and, after drying over sodium sulphate, evaporated at 40°C/12 mmHg with the addition of 400 ml of absolute toluene. The dark, glassy residue (ca 47 g) is chromatographed on 750 g of Kieselgel ("Merck"; 0.2–0.5 mm) with benzene/ethyl acetate (5:1 parts by volume). The almost colorless eluates are combined and evaporated at 40°C mmHg. The residue is recrystallized once from diethyl ether. 26.5 g of L-3-[1-(benzyloxy)-formamido]-6,7-dihydroxyhydrocoumarin is obtained as colorless crystals of melting point 148°–150°C.; $[\alpha]_D^{25} = -48.0°$ (c = 1%, ethanol). A further 1.1 g of melting point 144°–146°C. can be isolated from the mother liquor; $[\alpha]_D^{25} = -47.0°$ (c = 1%, ethanol).

EXAMPLE 8

77 g of 3-(3,4-dihydroxyphenyl)-L-alanine is added with stirring in an argon atmosphere to a suspension of 140 g of borax in 700 ml of water. The mixture is stirred for 15 minutes and then brought to pH 9 (pH meter) with 2-N aqueous sodium hydroxide. A boric acid complex forms in which the hydroxyl groups on the phenyl ring of the alanine derivative are esterified with boric acid. 77 g of chloroformic acid benzyl ester is subsequently added in portions of about 4 ml in the course of three hours at a temperature between 0°C. and 10°C., the pH of the mixture being held between 9 and 9.5 by the addition of 2-N sodium hydroxide. After the addition, the mixture is cooled to 0°C. and filtered off from a small amount of undissolved material, and the filtrate is extracted twice with 500 ml of diethyl ether each time. The ether extracts are washed once with 100 ml of water and then discarded. The aqueous alkaline extracts are brought to pH 1 with 6-N aqueous sulphuric acid with ice-cooling and then extracted twice with 1,000 ml of diethyl ether each time. The organic extracts are washed four times with 500 ml of water each time, then combined and, after drying over sodium sulphate and animal charcoal, evaporated under vacuum with the addition of toluene. 125.7 g of crude N-benzyloxycarbonyl-3-(3,4-dihydroxyphenyl)-L-alanine is thus obtained as a weakly violet-colored glass; $[\alpha]_D^{25} = +1.5°$ (c = 1.935%, methanol).

EXAMPLE 9

16.2 g of iodoso-benzene diacetate is added in one portion in an argon atmosphere to a solution of 29.7 g of N-(tertbutoxycarbonyl)-3-(3,4-dihydroxyphenyl)-L-alanine in 200 ml of glacial acetic acid. 0.2 g of p-tolunesulphonic acid is then added, the temperature rising to 27°C. After 20 hours at room temperature, the deep-red colored mixture is evaporated at 40°C/12 mmHg and re-evaporated once with the addition of toluene. The glassy residue is dissolved in 300 ml of diethyl ether, filtered and successively washed twice with 100 ml of water each time, twice with 100 ml of saturated aqueous sodium bicarbonate solution each time and twice with 50 ml of water each time. The organic phase is dried over sodium sulphate/active charcoal and evaporated at 40°C/12 mmHg. After the recrystallization from toluene/diethyl ether, the crystalline residue yields 7.9 g of L-3-(tertbutoxyformamido)-6,7-dihydroxyhydrocoumarin of melting point 173°–176°C. (decomposition) which is identical with the product manufactured without the use of p-toluenesulphonic acid as a catalyst.

EXAMPLE 10

16.1 g of iodoso-benzene diacetate is added in one portion in an argon atmosphere to a solution, which has been cooled to 0°C., of 33.1 g of N-benzyloxycarbonyl)-3-(3,4-dihydroxyphenyl)-L-alanine in 100 ml of absolute tetrahydrofuran and 150 ml of formic acid (99% by wt.). The solution immediately becomes black-red in color and the temperature rises to 10°C. The mixture is stirred for 1 hour with ice-cooling and then for 1 hour at room temperature. It is then evaporated at 40°C/12 mmHg with the addition of toluene. The residue is taken up in 300 ml of ethyl acetate, filtered and the filtrate successively washed twice with 100 ml of water each time, twice with 100 ml of saturated aqueous sodium bicarbonate solution each time and twice with 50 ml of water each time. The organic phase is dried over sodium sulphate/active charcoal, and evaporated at 40°C/12 mmHg. After two recrystallizations from diethyl ether/petroleum ether (B.P.40°–60°), there is obtained 7.2 g of L-3-[1-benzyloxy)formamido]-6,7-dihydroxyhydrocoumarin of melting point 143°-146°C. (decomposition) which is identical with the product manufactured in glacial acetic acid.

EXAMPLE 11

11.6 g of silver oxide and 25 g of sodium sulphate are introduced in portions within ca 10 minutes, with ice-water cooling and stirring in an argon atmosphere, into 16.55 g of N-(benzyloxycarbonyl)-3-(3,4-dihydroxyphenyl)-L-alanine in 250 ml of glacial acetic acid. After 24 hours at room temperature, the mixture is filtered, and the filtrate is evaporated at 40°C/12 mmHg. The residue is taken up in 500 ml of ethyl acetate, washed three times with 100 ml of saturated aqueous sodium bicarbonate solution each time and three times with 100 ml of saturated aqueous sodium chloride solution each time, and the organic phase is dried over sodium sulphate and a large amount of active charcoal. It is then evaporated at 40°C/12 mmHg with the addition of toluene. The residue is chromatographed on 200 g of Kieselgel ("Merck": 0.2–0.5 mm) with chloroform/isopropanol (10:0.5 parts by volume. The fractions containing the desired product are combined and evaporated at 40°C/ 12 mmHg. After one recrystallization from diethyl ether, there is obtained 2 g of L-3-[1-(benzyloxy)-formamido]-6,7-dihydroxyhydrocoumarin of melting point 146°–148°C. The substance is identical with that obtained from N-(benzyloxycarbonyl)-3-(3,4-dihydroxyphenyl)-L-alanine by oxidation with iodoso-benzene diacetate.

EXAMPLE 12

A solution of 8.1 g of L-3-(tertbutoxyformamido)-6,7-dihydroxyhydrocoumarin in 27.7 ml of acetic anhydride and 42 ml of absolute pyridine is stirred at room temperature for 48 hours. After the addition of toluene, the mixture is concentrated at 40°C/12 mmHg, and the residue is partitioned between 300 ml of ethyl acetate and 150 ml of ice-cold aqueous 0.4-N hydrochloric acid. The organic phase is washed once with 300 ml of ice-cold aqueous 0.4-N hydrochloric acid, once with 300 ml of water and once with saturated aqueous sodium bicarbonate solution. The ethyl acetate phase is dried over sodium sulphate/active charcoal and evaporated at 40°C/12 mmHg with the addition of toluene. After one recrystallization from toluene, there is obtained 6.7 g of L-3-(1-tertbutoxyformamido)-6,7-diacetoxyhydrocoumarin of melting point 127°–130°C; $[\alpha]_D^{25} = -4.8°$ (c=1%, tetrahydrofuran).

EXAMPLE 13

6.95 g of L-3-(1-tertbutoxyformamido)-6,7-diacetoxyhydrocoumarin is dissolved in 135 ml of ethyl acetate. On introduction of dry hydrogen chloride gas for 3 hours with ice-cooling, a gelatinous precipitate forms. The mixture is subsequently allowed to stand at room temperature for a further 30 minutes, then filtered off by suction and rinsed with absolute ethyl acetate. The colorless crystals are dried in a high vacuum over phosphorus pentoxide/potassium hydroxide. There is obtained 4.65 g of L-6,7-diacetoxy-3-aminohydrocoumarin hydrochloride of melting point 209°–211°C.; $[\alpha]_D^{25} = -19.8°$(c = 0.5%, water).

EXAMPLE 14

A strong stream of dry hydrogen chloride gas is conducted with ice-cooling for 30 minutes into a solution of 7.5 g of L-3-(1-tertbutoxyformamido)-6,7-dihydroxyhydrocoumarin in 150 ml of ethyl acetate and 50 ml of absolute toluene, which causes the immediate precipitation of colorless crystals. The mixture is held at room temperature for 20 hours and then at −19°C. for 16 hours. The crystals are filtered off and successively washed with 30 ml of ethyl acetate, 50 ml of ethyl acetate/diethyl ether (1:1 parts by volume) and 100 ml of diethyl ether and dried. There is obtained 5.4 g of crude L-3-amino-6,7-dihydroxyhydrocoumarin hydrochloride of melting point 263°–264°C. (decomposition); $[\alpha]_D^{25} = -38.4°$(c=1%, methanol).

EXAMPLE 15

14.5 g of L-3-[1-benzyloxy)-formamido]-6,7-dihydroxyhydrocoumarin is dissolved in 350 ml of glacial acetic acid (analytical grade) and hydrogenated over 3.5 g of palladium-on-charcoal (5%) under normal pressure at room temperature. After completion of the hydrogen untake (ca 2 hours), the catalyst is filtered off in an argon gas atmosphere. 38.6 ml of a 5% by weight solution of hydrogen chloride in glacial acetic acid is added to the filtrate at 40°C., immediately precipitating a colorless crystalline precipitate. After 14 hours at room temperature, the crystals are filtered off, washed with 100 ml of glacial acetic acid and then with 100 ml of diethyl ether and dried. 8.7 g of crude L-3-amino-6,7-dihydroxyhydrocoumarin hydrochloride of melting point 265°–267°C. (decomposition) is isolated; $[\alpha]_D^{25} = -36.0°$ (c = 1%, methanol).

The product obtained is recrystallized from formic acid/diethyl ether or from methanol/diethyl ether to yield a product of melting point 263°–264°C. (decomposition); $[\alpha]_D^{25} = -39°$(c = 1.039%, methanol).

EXAMPLE 16

A solution of 6.7 g of L-3-amino-6.7-dihydroxyhydrocoumarin hydrochloride in 100 ml of oxygen-free water is heated to boiling for 10 minutes in a nitrogen atmosphere and then concentrated to a volume of ca 30 ml. 6.7 ml of propylene oxide and 7 ml of oxygen-free acetonitrile are added to the concentrated solution. After 2 hours, the solution has a pH of ca 4.5, and colorless crystals begin to precipitate. The mixture is held at 4°C. for 24 hours. The almost colorless 3-(2,4,5-trihydroxyphenyl)-L-alanine is then filtered off and successively washed twice with 30 ml of absolute ethanol each time and twice with 50 ml of diethyl ether each time and dried. There is obtained 4.2 g of the desired product of melting point 252°–253°C. (decomposition); $[\alpha]_D^{25} = -12.4°$ [C=2%,1-N hydrochloric acid/methanol (1:1 parts by volume)].

EXAMPLE 17

34.8 g of iodoso-benzene diacetate and 442 mg of p-toluenesulphonic acid are added in one portion with stirring in an argon atmosphere to a solution of 41 g of N-benzyloxycarbonyl-D,L-α-methyl-3,4-dihydroxyphenylalanine in 540 ml of glacial acetic acid. The resulting dark-red solution is subsequently stirred at 25°C. for 16 hours and then concentrated at 40°C/12 mmHg. The residue is taken up in 400 ml of ethyl acetate, cooled to 0°C. and successively washed twice with 200 ml of ice-cold saturated aqueous sodium chloride solution each time, four times with 200 ml of ice-cold saturated aqueous sodium bicarbonate solution each time and twice with 200 ml of ice-cold saturated aqueous sodium chloride solution each time. The aqueous phases are back-extracted once with 400 ml of ethyl acetate and then discarded. The organic phases are combined and, after drying over sodium sulphate, concentrated at 40°C/12 mmHg. The residue (27 g of dark crystals) is chromatographed on 1,000 g of silica gel (Merck). The D,L-3-[-1-(benzyloxy)-formamido]-3-methyl-6,7-dihydroxyhydrocoumarin is eluted with benzene/ethyl acetate (8:2 parts by volume). After one recrystallization from ethyl acetate, there is obtained 19.1 g of colorless crystals with a melting point of 190°–192°C. (decomposition).

EXAMPLE 18

Utilizing the procedure of Example 8, α-methyl-3-(3,4-dihydroxyphenyl)-D,L-alanine can be converted to N-benzyloxycarbonyl-α-methyl-3-(3,4-dihydroxyphenyl-D,L-alanine.

EXAMPLE 19

23.7 g of iodoso-benzene diacetate is added in an argon atmosphere to a solution of 16 g of D,L-α-methyl-3-(3,4-dihydroxyphenyl)-propionic acid in 300 ml of glacial acetic acid, and the mixture is allowed to stand at room temperature for 20 hours with occasional shaking. The mixture is thereupon evaporated at a bath-temperature of 40°C. The brown oily residue is dissolved in 500 ml of tetrahydrofuran/ethyl acetate (2:3 parts by volume) and then successively washed once with 200 ml of saturated aqueous sodium chloride solution, three times with 100 ml of saturated aqueous sodium bicarbonate solution each time and once with 100 ml of saturated aqueous sodium chloride solution. All the aqueous phases are back-extracted once with 500 ml of tetrahydrofuran/ethyl acetate (2:3 parts by volume) and then discarded. The organic phases are combined and dried over sodium sulphate and animal charcoal. The mixture is then filtered off, rinsed with tetrahydrofuran and evaporated under vacuum. The residue is treated with toluene, and then once more evaporated. There is obtained 6.2 g of a black oil. This oil is heated on a steam-bath three times with 250 ml of high-boiling petroleum ether (B.P.80°–120°) each time, and then the petroleum ether is decanted off and discarded. The residue is again evaporated, and there is obtained 2.8 g of a black oil. These 2.8 g of crude product is dissolved in 95 ml of absolute pyridine. 5.9 g of acetic anhydride is then added and the mixture is allowed to stand at room temperature under argon for 60 hours. The brown solution is then evaporated under vacuum at a bath-temperature of 30°C. The oily residue is dissolved in 200 ml of ethyl acetate and successively washed twice with 50 ml of water each time, twice with 50 ml of 2-N sulphuric acid each time, twice with 50 ml of water each time, once with 50 ml of saturated aqueous sodium bicarbonate solution and once with 50 ml of water. All the aqueous phases are back-extracted once with 200 ml of ethyl acetate and then discarded. The organic phases are combined and dried over sodium sulphate and animal charcoal. The mixture is thereupon filtered off, rinsed with ethyl acetate and evaporated in a vacuum with the addition of toluene. The residue is subsequently again treated with toluene and evaporated. There is obtained 3 g of a black oil which is chromatographed on 90% of Kieselgel with benzene/ethyl acetate. The product prepurified in this way is recrystallized from diethyl ether/petroleum ether. There is obtained 0.3 g of D,L-6,7-diacetoxy-3-methylhydrocoumarin with a melting point of 104°–105°C.

EXAMPLE 20

15 ml of benzoyl chloride is slowly added dropwise, with stirring and ice-cooling, to a mixture of 19.53 g of L-3-(tertbutoxyformamido)-6,7-dihydroxyhydrocoumarin, 100 ml of absolute pyridine and 17.9 ml of triethylamine, and the resulting mixture is stirred at room temperature for a further 48 hours. It is then evaporated under reduced pressure at a bath-temperature of 30°C. with the addition of toluene. The residue is partitioned between 1 liter of ethyl acetate and 400 ml of ice-cold 0.4-N hydrochloric acid and the aqueous phase is extracted with 1 liter of ethyl acetate. The combined ethyl acetate extracts are successively washed once with 600 ml of ice-cold 0.4-N hydrochloric acid, twice with 200 ml of saturated aqueous sodium bicarbonate solution each time and once with saturated aqueous sodium chloride solution. The organic phase is dried over sodium sulphate/animal charcoal, and the filtrate is evaporated under reduced pressure at a bath-temperature of 30°C. The evaporation residue is recrystallized from isopropyl ether. There is thus obtained L-3-(tertbutoxyformamido)-6,7-dibenzoyloxyhydrocoumarin of melting point 146°–148°C.

EXAMPLE 21

13.57 g of L-3-(tertbutoxyformamido)-6,7-dibenzoyloxyhydrocoumarin is dissolved in 280 ml of absolute ethyl acetate. Dry hydrogen chloride gas is led into this solution for 4 hours. The solution is subsequently evaporated under reduced pressure and then re-evaporated twice with the addition of toluene. The crystalline residue is thoroughly triturated with isopropyl ether. There is thus obtained L-3-amino-6,7-bisbenzoyloxyhydrocoumarin hydrochloride of melting point 219°–221°C; $[\alpha]_D^{25} = -8.2°(c=0.5\%$, glacial acetic acid).

EXAMPLE 22

14.5 g of iodoso-benzene diacetate is added with stirring to a solution of 16.9 g of D,L-N-benzyloxycarbonyl-2,3,3-trimethyldopa in 2,000 ml of ethyl acetate. The solution rapidly becomes dark in color. After 10 minutes, 5 ml of boron trifluoride etherate is added. The mixture is stirred for 6 hours at room temperature, then washed with a 10% by weight aqueous potassium bicarbonate solution, and the ethyl acetate phase is dried over magnesium sulphate and concentrated. The remaining 18.5 g of crude, oily residue is chromatographed on Kieselgel with, as the eluting agent, benzene/methanol (4:1 parts by volume). There is thus obtained 6.5 g of pure D,L-3,4,4-trimethyl-3-N-benzyloxycarbonylamino-6,7-dihydroxyhydrocoumarin, which can be recrystallized from diethyl ether melting point 136°–138°C.

EXAMPLE 23

Utilizing the procedure of Example 8, 2,3,3-trimethyldopa can be converted to D,L-N-benzyloxycarbonyl-2,3,3-trimethyldopa, having a melting point of 194°–197°C.

EXAMPLE 24

6.5 g of D,L-6,7-dihydroxy-3-N-benzyloxycarbonylamino-3,4,4-trimethylhydrocoumarin is stirred overnight at room temperature with 50 ml of pyridine and 50 ml of acetic anhydride. The mixture is then concentrated under vacuum, the residue taken up in 0.5-N hydrochloric acid and extracted with chloroform. The organic phase is washed with a 10% by weight aqueous potassium bicarbonate solution, dried over magnesium sulphate and concentrated. The dark oil (7.1 g) which is thus obtained is chromatographed on Kieselgel, with, as the eluting agent; benzene/acetonitrile (19:1 parts by volume). 5.5 g of pure D,L-6,7-diacetoxy-3-N-benzyloxycarbonylamino-3,4,4-trimethylhydrocoumarin is thus obtained as a pale yellow oil.

EXAMPLE 25

3.1 g of D,L-6,7-diacetoxy-3-N-benzyloxycarbonylamino-3,4,4-trimethylhydrocoumarin, dissolved in 100 ml of glacial acetic acid, is hydrogenated under normal pressure at room temperature in the presence of 0.5 g of palladium on active charcoal. The hydrogen uptake is completed after 0.5 hour. After the addition of 0.86 g of benzyl chloride, the solution is hydrogenated again, the catalyst is then filtered off, the filtrate is concentrated, and the residue is recrystallized from isopropanol. 2.2 g of D,L-6,7-diacetoxy-3-amino-3,4,4-trimethylhydrocoumarin is obtained as a colorless crystalline product of melting point 201°–206°C. (decomposition).

The following examples illustrate pharmaceutical preparations containing the novel coumarin derivatives provided by the invention.

EXAMPLE 26

Tablets of the following composition are prepared in a conventional manner:

| | |
|---|---|
| L-6,7-diacetoxy-3-aminohydrocoumarin | 100 mg |
| lactose | 61 mg |
| corn starch | 30 mg |
| polyvinylpyrrolidone | 4 mg |
| talc | 5 mg |

EXAMPLE 27

Gelatin capsules containing the following ingredients are prepared in a conventional manner:

| | |
|---|---|
| L-3-(1-tertbutoxyformamido)-6,7-dihydroxyhydrocoumarin | 50 mg |
| mannitol | 98.5 mg |
| stearic acid | 1.5 mg |

We claim:
1. L-3-formamido-6,7-dihydroxyhydrocoumarin.
2. L-3-(1-tertbutoxyformamido)-6,7-diacetoxyhydrocoumarin.
3. L-3-acetamido-6,7-dihydroxyhydrocoumarin.
4. L-3-[1-tertbutoxyformamido]-6,7-dihydroxyhydrocoumarin.

* * * * *